US006689103B1

(12) United States Patent
Palasis

(10) Patent No.: US 6,689,103 B1
(45) Date of Patent: Feb. 10, 2004

(54) INJECTION ARRAY APPARATUS AND METHOD

(75) Inventor: Maria Palasis, Wellesley, MA (US)

(73) Assignee: SciMed Life System, Inc., Maple Grove, MN (US)

( * ) Notice: Subject to any disclaimer, the term of this patent is extended or adjusted under 35 U.S.C. 154(b) by 0 days.

(21) Appl. No.: 09/457,453

(22) Filed: Dec. 8, 1999

Related U.S. Application Data
(60) Provisional application No. 60/133,122, filed on May 7, 1999.

(51) Int. Cl.[7] ................................................. A61N 5/00
(52) U.S. Cl. ........................ 604/173; 604/272; 606/186
(58) Field of Search ............................. 604/35, 40, 42, 604/44, 158, 164.61, 164.09, 169.11, 164.13, 173, 264, 272, 523, 524–528, 533–535; 606/151, 167, 181–184, 185, 186; 607/120, 126

(56) References Cited

U.S. PATENT DOCUMENTS

| | | | |
|---|---|---|---|
| 1,934,046 A | * 11/1933 | Demarchi | 604/115 |
| 2,551,902 A | * 5/1951 | Rieck | 604/173 |
| 4,397,903 A | * 8/1983 | Allen et al. | 428/156 |
| 4,578,061 A | 3/1986 | Lemelson | 604/164 |
| 4,596,556 A | 6/1986 | Morrow et al. | 604/70 |
| 4,790,824 A | 12/1988 | Morrow et al. | 604/143 |
| 5,064,413 A | 11/1991 | McKinnon et al. | 604/70 |
| 5,098,389 A | 3/1992 | Cappucci | 604/158 |
| 5,236,424 A | 8/1993 | Imran | 604/280 |
| 5,262,128 A | 11/1993 | Leighton et al. | 422/100 |
| 5,311,841 A | * 5/1994 | Thaxton | 604/506 |
| 5,324,276 A | 6/1994 | Rosenberg | 604/269 |
| 5,354,279 A | 10/1994 | Hofling | 604/164 |
| 5,383,851 A | 1/1995 | McKinnon, Jr. et al. | 604/68 |
| 5,399,163 A | 3/1995 | Peterson et al. | 604/68 |
| 5,403,311 A | 4/1995 | Abele et al. | 606/49 |
| 5,417,683 A | * 5/1995 | Shiao | 606/1 |

(List continued on next page.)

FOREIGN PATENT DOCUMENTS

| | | |
|---|---|---|
| DE | 196 07 922 A1 | 9/1997 |
| EP | 0 934 728 A2 | 8/1999 |
| WO | WO 92/10142 A1 | 6/1992 |
| WO | WO 92/10142 | 6/1992 |
| WO | WO 98/05307 A1 | 2/1998 |
| WO | WO 99/04851 | 2/1999 |
| WO | WO 99/39624 A1 | 8/1999 |
| WO | WO 99/44524 | 9/1999 |
| WO | WO 99/48545 A1 | 9/1999 |
| WO | WO 99/49926 | 10/1999 |

OTHER PUBLICATIONS

"Chemical Engineers Develop Microneedles for Painfree Injections," Dec. 1998, one page, source unknown.
Internet Article, 'Taking the "Ouch" Out of Needles: Arrays of Micron–Scale "Microneedles" Offer New Technique For Drug Delivery', John Toon, Released Jun. 22, 1998, 4 pgs.

*Primary Examiner*—An H. Thanh
(74) *Attorney, Agent, or Firm*—Kenyon & Kenyon

(57) ABSTRACT

A fluid delivery system for delivering and injecting fluid into heart tissue, or other organ tissues. The fluid delivery system includes an injection catheter disposed in an elongate sheath. A nozzle, including an injection array, is disposed adjacent the distal end of the injection catheter. In a first (microneedle) embodiment, the injection array comprises a plurality of microneedles each defining an injection lumen in fluid communication with the lumen of the catheter. In a second (needle-less) embodiment, the injection array comprises a plurality of injection lumens in fluid communication with the lumen of the catheter. Fluid is transferred to the injection lumen array from a fluid source through the lumen in the catheter. The injection lumen array distributes the fluid at the injection site over a greater area than would otherwise be achieved with a single needle injection. Thus, the injection lumen array improves fluid retention in the tissue at the injection site.

19 Claims, 6 Drawing Sheets

U.S. PATENT DOCUMENTS

| | | | |
|---|---|---|---|
| 5,419,777 A | 5/1995 | Hofling | 604/264 |
| 5,457,041 A | 10/1995 | Ginaven et al. | 435/172.1 |
| 5,464,395 A | 11/1995 | Faxon et al. | 604/96 |
| 5,472,441 A | 12/1995 | Edwards et al. | 606/41 |
| 5,478,328 A | 12/1995 | Silverman et al. | 604/272 |
| 5,520,639 A | 5/1996 | Peterson et al. | 604/68 |
| 5,538,504 A | 7/1996 | Linden et al. | 604/53 |
| 5,651,774 A * | 7/1997 | Taranto et al. | 604/198 |
| 5,672,174 A | 9/1997 | Gough et al. | 606/41 |
| 5,674,208 A | 10/1997 | Berg et al. | 604/527 |
| 5,693,029 A | 12/1997 | Leonhardt | 604/264 |
| 5,697,901 A | 12/1997 | Eriksson | 604/46 |
| 5,702,384 A | 12/1997 | Umeyama et al. | 604/892.1 |
| 5,766,164 A | 6/1998 | Mueller et al. | 606/15 |
| 5,782,823 A | 7/1998 | Mueller | 606/7 |
| 5,807,395 A | 9/1998 | Mulier et al. | 606/41 |
| 5,830,222 A | 11/1998 | Makower | 606/159 |
| 5,840,061 A | 11/1998 | Menne et al. | 604/68 |
| 5,843,017 A | 12/1998 | Yoon | 604/22 |
| 5,882,332 A | 3/1999 | Wijay | 604/508 |
| 5,997,525 A | 12/1999 | March et al. | 604/508 |
| 6,063,082 A | 5/2000 | DeVore et al. | 606/45 |
| 6,093,185 A | 7/2000 | Ellis et al. | 606/28 |
| 6,203,556 B1 | 3/2001 | Evans et al. | 606/185 |
| 6,302,870 B1 | 10/2001 | Jacobsen et al. | 604/272 |

* cited by examiner

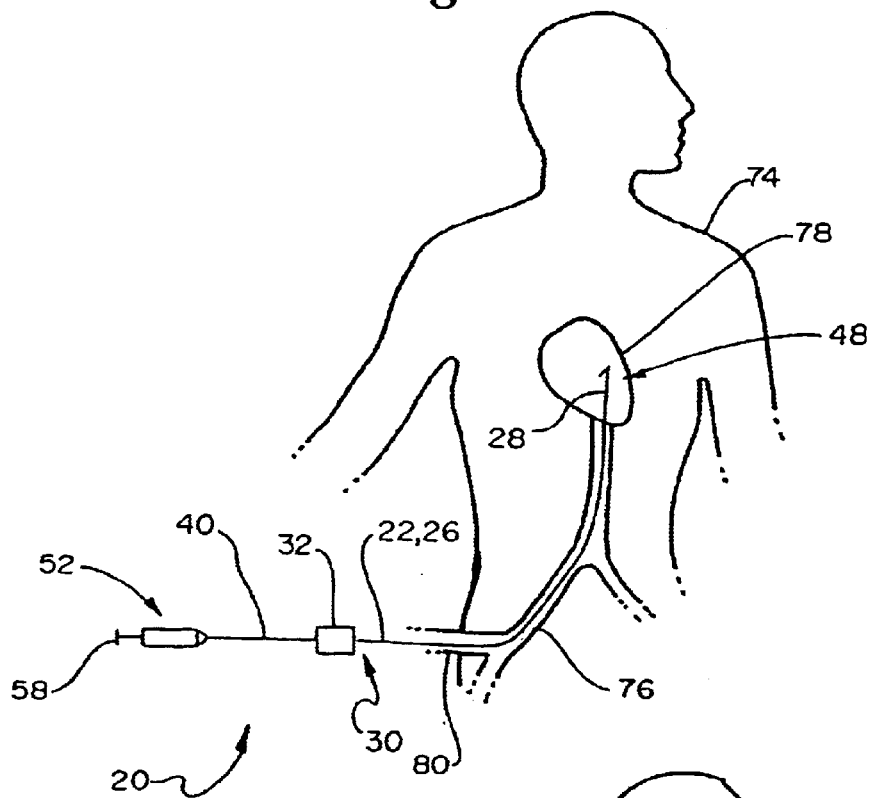
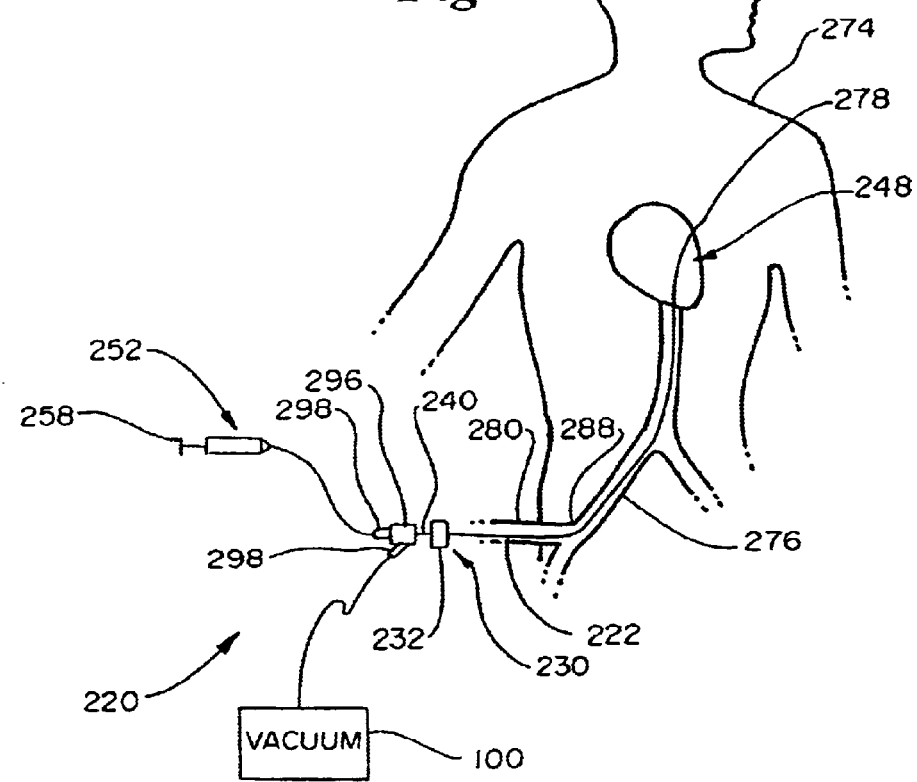

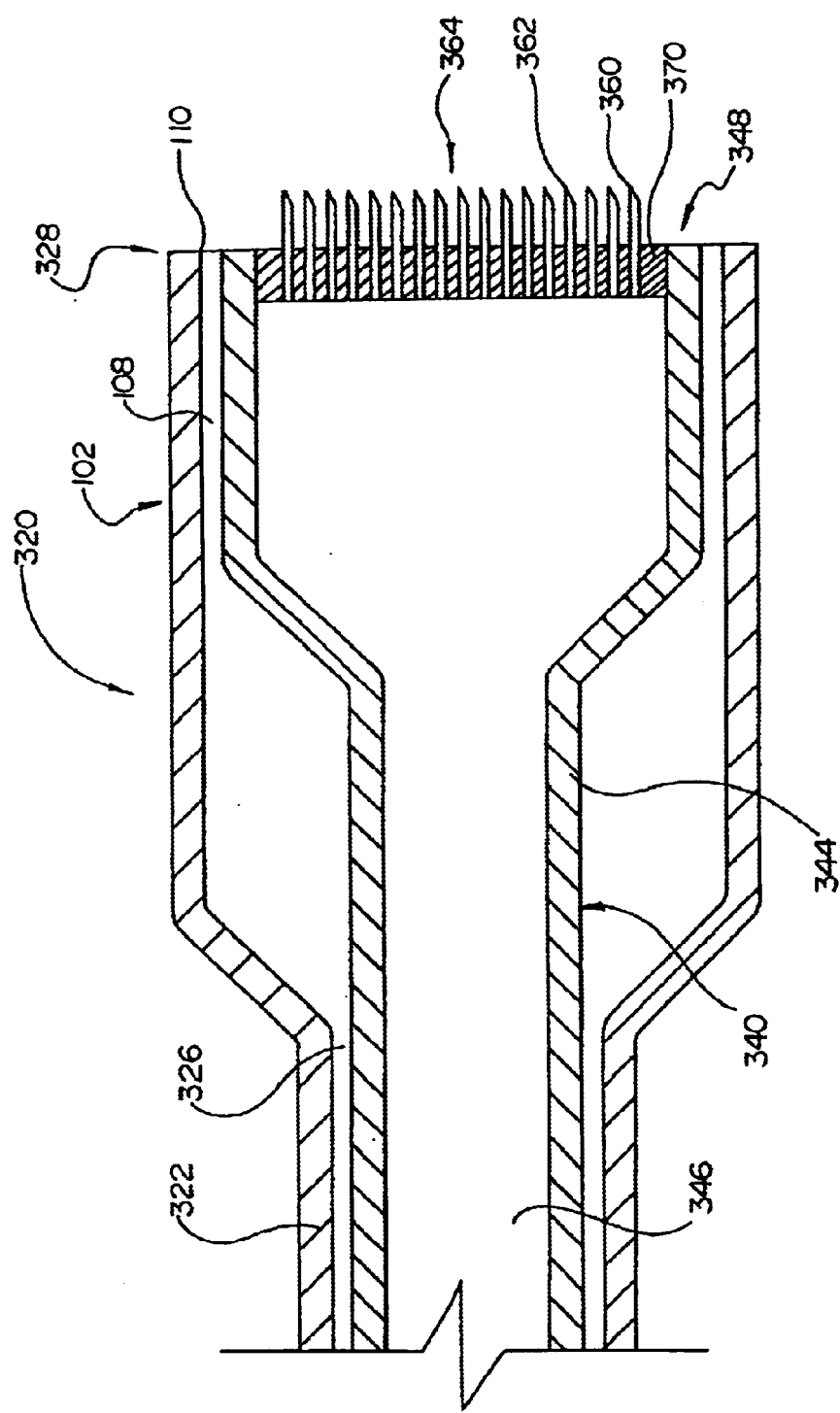

INJECTION ARRAY APPARATUS AND METHOD

RELATED APPLICATIONS

This application claims the benefit of Provisional Patent Application Ser. No. 60/133,122, filed May 7, 1999, entitled INCREASED EFFICIENCY DIRECT INJECTION OF THERAPEUTIC AGENTS, which is hereby incorporated by reference.

This application is related to patent application Ser. No. 09/457,254 filed on Dec. 8, 1999, entitled LATERAL NEEDLE INJECTION APPARATUS AND METHOD, now U.S. Pat. No. 6,319,230; patent application Ser. No. 09/457,193, filed on Dec. 8, 1999, entitled LATERAL NEEDLE-LESS INJECTION APPARATUS AND METHOD; and patent application Ser. No. 09/456,456, filed on Dec. 8,1999, entitled NEEDLE-LESS INJECTION APPARATUS AND METHOD, now U.S. Pat. No. 6,344,027.

FIELD OF THE INVENTION

The present invention generally relates to delivering and injecting fluid into heart tissue. More specifically, the present invention relates to delivering and injecting fluid into heart tissue utilizing an injection array.

BACKGROUND OF THE INVENTION

Injection catheters may be used to inject therapeutic or diagnostic agents into a variety of organs, such as the heart. In the case of injecting a therapeutic agent into the heart, 27 or 28 gauge needles are generally used to inject solutions carrying genes, proteins, or drugs directly into the myocardium. A typical volume of an agent delivered to an injection site is about 100 microliters. A limitation to this method of delivering therapeutic agents to the heart is that the injected fluid tends to leak and/or disperse from the site of the injection after the needle is disengaged from the heart. In fact, fluid may continue to leak over several seconds. In the case of dynamic organs such as the heart, there may be more pronounced leakage with each muscle contraction.

Therapeutic and diagnostic agents may be delivered to a portion of the heart as part of a percutaneous myocardial revascularization (PMR) procedure. PMR is a procedure which is aimed at assuring that the heart is properly oxygenated. Assuring that the heart muscle is adequately supplied with oxygen is critical to sustaining the life of a patient. To receive an adequate supply of oxygen, the heart muscle must be well perfused with blood. In a healthy heart, blood perfusion is accomplished with a system of blood vessels and capillaries. However, it is common for the blood vessels to become occluded (blocked) or stenotic (narrowed). A stenosis may be formed by an atheroma which is typically a harder, calcified substance which forms on the walls of a blood vessel.

Historically, individual stenotic lesions have been treated with a number of medical procedures including coronary bypass surgery, angioplasty, and atherectomy. Coronary bypass surgery typically involves utilizing vascular tissue from another part of the patient's body to construct a shunt around the obstructed vessel. Angioplasty techniques such as percutaneous transluminal angioplasty (PTA) and percutaneous transluminal coronary angioplasty (PTCA) are relatively non-invasive methods of treating a stenotic lesion. These angioplasty techniques typically involve the use of a guide wire and a balloon catheter. In these procedures, a balloon catheter is advanced over a guide wire such that the balloon is positioned proximate a restriction in a diseased vessel. The balloon is then inflated and the restriction in the vessel is opened. A third technique which may be used to treat a stenotic lesion is atherectomy. During an atherectomy procedure, the stenotic lesion is mechanically cut or abraded away from the blood vessel wall.

Coronary by-pass, angioplasty, and atherectomy procedures have all been found effective in treating individual stenotic lesions in relatively large blood vessels. However, the heart muscle is perfused with blood through a network of small vessels and capillaries. In some cases, a large number of stenotic lesions may occur in a large number of locations throughout this network of small blood vessels and capillaries. The torturous path and small diameter of these blood vessels limit access to the stenotic lesions. The sheer number and small size of these stenotic lesions make techniques such as cardiovascular by-pass surgery, angioplasty, and atherectomy impractical.

When techniques which treat individual lesion are not practical, percutaneous myocardial revascularization (PMR) may be used to improve the oxygenation of the myocardial tissue. A PMR procedure generally involves the creation of holes, craters or channels directly into the myocardium of the heart. In a typical PMR procedure, these holes are created using radio frequency energy delivered by a catheter having one or more electrodes near its distal end. After the wound has been created, therapeutic agents are sometimes ejected into the heart chamber from the distal end of a catheter.

Positive clinical results have been demonstrated in human patients receiving PMR treatments. These results are believed to be caused in part by blood flowing within the heart chamber through channels in myocardial tissue formed by PMR. Increased blood flow to the myocardium is also believed to be caused in part by the healing response to wound formation. Specifically, the formation of new blood vessels is believed to occur in response to the newly created wound. This response is sometimes referred to as angiogenesis. After the wound has been created, therapeutic agents which are intended to promote angiogenesis are sometimes injected into the heart chamber. A limitation of this procedure is that the therapeutic agent may be quickly carried away by the flow of blood through the heart.

In addition to promoting increased blood flow, it is also believed that PMR improves a patient's condition through denervation. Denervation is the elimination of nerves. The creation of wounds during a PMR procedure results in the elimination of nerve endings which were previously sending pain signals to the brain as a result of hibernating tissue.

Currently available injection catheters are not particularly suitable for accurately delivering small volumes of therapeutic agents to heart tissue. Improved devices and methods are desired to address the problems associated with retention of the agent in the heart tissue as discussed above. This is particularly true for agents carrying genes, proteins, or other angiogenic drugs which may be very expensive, even in small doses.

SUMMARY OF THE INVENTION

The present invention provides an improved apparatus and method for delivering and injecting fluid into heart tissue, or other organ tissues such as liver tissue, bladder tissue, etc. The present invention addresses the problems associated with retention of the fluid in the tissue by utilizing an injection array, such as a plurality of microneedles or a plurality of injection lumens. The present invention may be used to deliver genes, proteins, or drugs directly into the myocardium for purposes of myocardial revascularization.

In an exemplary embodiment, the present invention provides a fluid delivery system including an injection catheter disposed in an elongate sheath. A fluid source is connected to the proximal end of the injection catheter and is in fluid communication with the lumen of the catheter. A nozzle is disposed adjacent the distal end of the injection catheter. In a first embodiment, the nozzle includes a plurality of microneedles each defining an injection lumen in fluid communication with the lumen of the catheter. In a second embodiment, the nozzle defines a plurality of injection lumens in fluid communication with the lumen of the catheter. The first embodiment may be referred to as the "microneedle" embodiment and the second embodiment may be referred to as the "needle-less" embodiment.

The microneedles may each have a diameter in the range of approximately 0.005 to 0.05 inches, and a penetrating length in the range of approximately 0.5 to 5 mm. The injection lumens in the microneedle embodiment may have a diameter in the range of approximately 0.00005 to 0.005 inches. Similarly, the injection lumens in the needle-less embodiment may have a diameter in the range of approximately 0.00005 to 0.005 inches.

In both embodiments, the injection lumens collectively form an injection array terminating in a plurality of injection orifices. Fluid is transferred to the injection lumen array from the fluid source through the lumen in the catheter. The injection lumen array distributes the fluid at the injection site over a greater area than would otherwise be achieved with a single needle injection. Thus, the injection lumen array improves fluid retention in the tissue at the injection site.

Also in both embodiments, the catheter and/or sheath may be equipped with an anchor disposed adjacent the distal end thereof. The anchor may comprise a vacuum orifice in fluid communication with a vacuum source via a lumen in the catheter and/or sheath. The vacuum orifice is adapted to stabilize the distal end of the injection catheter and/or the distal end of the sheath.

The sheath may include a hood portion disposed at its distal end. The distal end of the injection catheter may be retracted within the hood of the sheath to reduce the probability that tissue damage will occur when the catheter is advanced through the vasculature of the patient.

The present invention also provides a method of delivering a fluid to heart tissue comprising the following steps. An injection catheter substantially as described above is inserted into a patient's body and navigated to the desired target site, for example, heart tissue such as the myocardium. The injection catheter may be navigated intravascularly or transthoracicly to the heart tissue. A sheath substantially as described above may also be advanced until its distal end is proximate the target site. The injection catheter is then advanced until the injection array is proximate the target tissue. Fluid is then urged out from the fluid source, through the lumen of the injection catheter, and into the heart tissue via the injection array. The injection lumen array distributes the fluid at the target site over a greater area thereby increasing retention of fluid in the heart tissue at the injection site.

Less than approximately 100 microliters of fluid may be injected into the heart tissue via the injection array. Approximately 0.1 to 20 microliters of fluid may be injected into the heart tissue via each injection lumen of the array. Due to the distribution of the injection array, a substantial amount if not all of the injected fluid is retained in the heart tissue.

BRIEF DESCRIPTION OF THE DRAWINGS

FIG. 4 is a schematic view of the fluid delivery system and a human patient;

FIG. 6 is a schematic view of the fluid delivery system and a human patient utilizing an anchor for stabilization;

FIG. 7 is a cross sectional view of the distal portion of the fluid delivery system incorporating a hood, shown in the extended position.

DETAILED DESCRIPTION OF THE INVENTION

The following detailed description should be read with reference to the drawings, in which like elements in different drawings are numbered identically. The drawings which are not necessarily to scale, depict selected embodiments and are not intended to limit the scope of the invention. Examples of constructions, materials, dimensions, and manufacturing processes are provided for various elements. Those skilled in the art will recognize that many of the examples provided have suitable alternatives which may be utilized.

Figure 1:
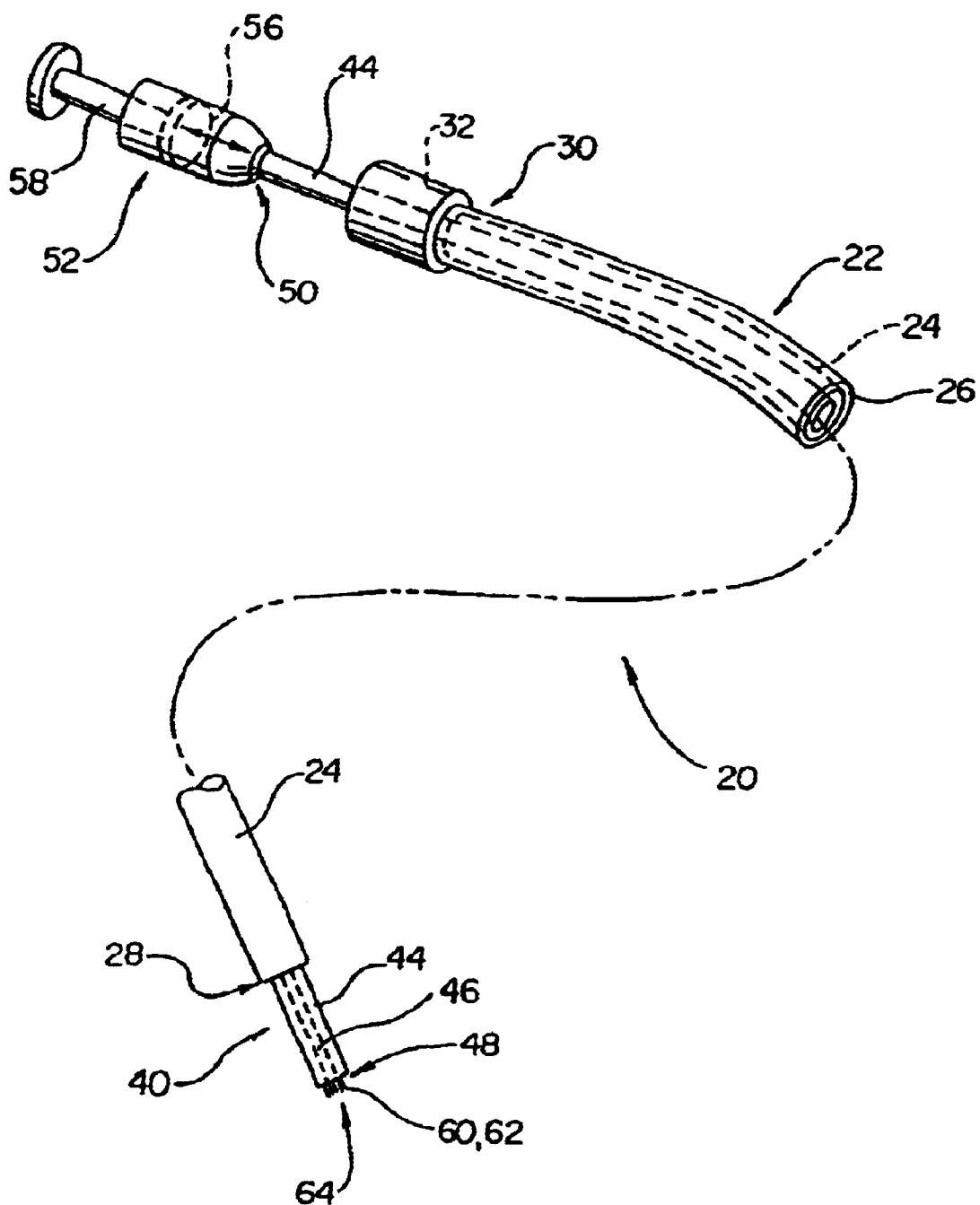
FIG. 1 is a perspective view of a fluid delivery system in accordance with the present invention.

FIG. 1 is a perspective view of a fluid delivery system 20 in accordance with the present invention. In the embodiment of FIG. 1, fluid delivery system 20 includes a sheath 22 comprising an elongate tubular member 24 defining a sheath lumen 26. Sheath 22 also includes a distal end 28 and a proximal end 30. A hub 32 is disposed at proximal end 30 of sheath 22.

Those of skill in the art will appreciate that sheath 22 may be comprised of many. materials without deviating from the spirit and scope of the present invention. Likewise, sheath 22 may be comprised of a single material, or a combination of materials. For example, sheath 22 may be a tube. In a presently preferred embodiment, the tube is comprised of PTFE (polytetrafluoroethylene). PTFE is a preferred material because it creates a smooth, low-friction surface for the passage of other devices through the sheath 22. Sheath 22 may also include a support member wound or braided around the tube. In a presently preferred embodiment, support member is comprised of a plurality of filaments. Filaments may be stainless steel wire. Those with skill in the art will appreciate that other embodiments of support member are possible without deviating from the spirit and scope of the present invention. For example, support member may be comprised of a woven polymer fabric. By way of a second example, support member may be comprised of polymer fibers arranged in a braided pattern.

Sheath 22 may be comprised of a polyether block amide (PEBA) using an extrusion process. Polyether block amide is commercially available from Atochem Polymers of Birdsboro, Pa. under the trade name PEBAX. In the extrusion process, molten PEBA is extruded onto the combined layers of inner tube 34 and support member. When this process is used, the extruded material fills interstitial spaces in support member. PEBA is extruded onto the combined layers of inner tube 34 and support member 36. When this process is used, the extruded material fills interstitial spaces in support member 36.

It is to be understood that other manufacturing processes can be used without departing from the spirit and scope of the present invention. Sheath 22 may also be comprised of other materials without departing from the spirit of scope of this invention.

Examples of materials which may be suitable in some applications include: polyethylene (PE), polypropylene (PP), polyvinylchloride (PVC), polyurethane, and polytetrafluoroethylene (PTFE).

Fluid delivery system 20 also includes an injection catheter 40 which is slidingly disposed in sheath lumen 26 of sheath 22. Injection catheter 40 includes an elongate tubular member 44 defining a lumen 46, a distal end 48, and a proximal end 50. A fluid source 52 is releasably connected to the proximal end 50 of injection catheter 40. Fluid source 52 in fluid communication with lumen 46 of elongate tubular member 44. Fluid source 52 is capable of injecting fluid into lumen 46 of elongate tubular member 44.

In the illustrated embodiment, fluid source 52 includes a variable volume chamber 56 in fluid communication with lumen 46 of elongate tubular member 44. Fluid source 52 further includes a plunger 58 slidingly disposed within variable volume chamber 56. Urging plunger 58 slidingly disposed within variable volume chamber 56. Urging plunger 58 distally has the effect of urging fluid into lumen 46 of elongate tubular member 55. A number of energy sources may be utilized to urge plunger 58 distally. Energy sources which may be suitable in some applications include springs, compressed gas, electricity, and manual forces. Fluid source 52 may alternatively comprise, for example, a conventional syringe or a high pressure injection system as disclosed in U.S. Pat. No. 5,520,639 to Peterson et al. which is hereby incorporated by reference.

Elongate tubular member 44 is moveable between a retracted position and an extended position wherein the distal end 48 of the injection catheter 40 extends beyond the distal end 28 of sheath 22. A plurality of microneedles 60 are disposed proximate the distal end 48 of injection catheter 40. Each microneedle 60 defines an injection lumen 62 in fluid communication with lumen 46 of elongate tubular member 44. Injection lumens 62 collectively form an injection lumen array 64.

Figure 2:
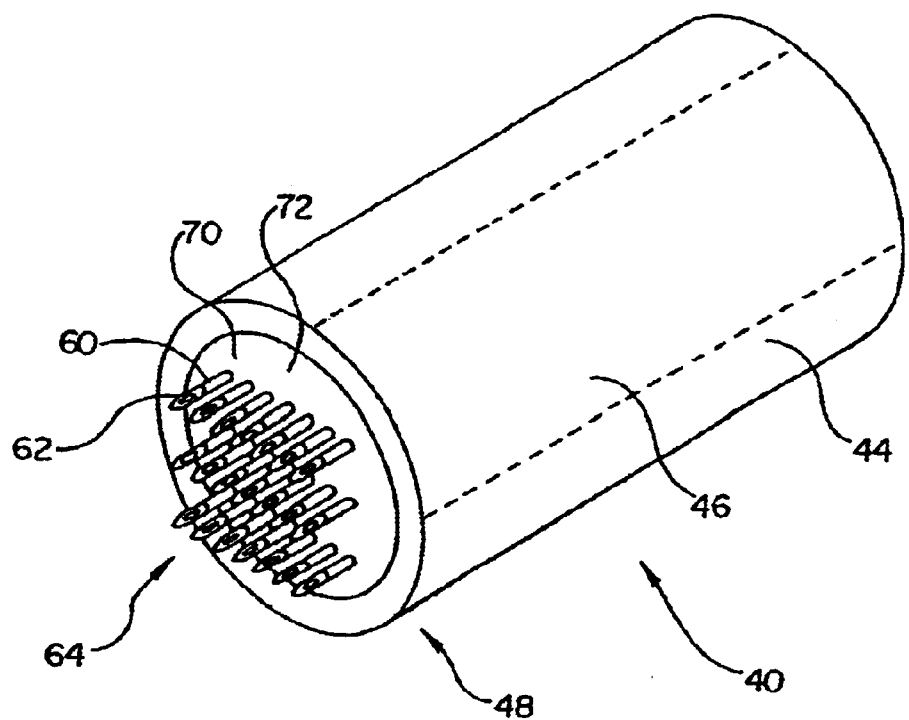
FIG. 2 is a perspective view of a first (microneedle) embodiment of the distal end of the injection catheter for use with the fluid delivery system illustrated in FIG. 1.

FIG. 2 is a detailed perspective view of the distal end 48 of the injection catheter 40 illustrating the microneedle embodiment in detail. A nozzle member 70 is disposed within lumen 46 proximate the distal end 48 of injection catheter 40. The microneedles 60 are disposed on a distal surface 72 of nozzle member 70. Microneedles 60 may be separate members inserted into holes defined in nozzle member 70 or may be an integral part of nozzle member 70. Nozzle member 70 and microneedles 60 define a plurality of injection lumens 62. Injection lumens 62 collectively form an injection lumen array 64. Each injection lumen 62 is in fluid communication with lumen 46 of elongate tubular member 44.

One embodiment of injection catheter 40 has been envisioned in which microneedles 60 and nozzle member 70 are both comprised of silicon. An example fabrication technique is described in U.S. Pat. No. 5,697,901 to Eriksson, which is hereby incorporated by reference. The microneedles 60 may each have a diameter in the range of approximately 0.005 to 0.05 inches, and a penetrating length in the range of approximately 0.5 to 5 mm. The injection lumens 62 in the microneedles 60 may have a diameter in the range of approximately 0.00005 to 0.005 inches. The microneedles 60 may be generally circular in cross section as shown. Those of skill in the art will appreciate that microneedles 60 may be other shapes without departing from the scope of the present invention. Examples of cross sectional shapes which may be suitable in some applications include oval, triangular, rectangular, square, and hexagonal.

Microneedles 60 and nozzle member 70 may be comprised of a variety of metallic and non-metallic materials. Examples of metallic materials which may be suitable in some applications include stainless steel, and nickel-titanium alloys, although it is recognized that any suitable metal or alloy may be utilized. Examples of non-metallic materials which may be suitable in some applications include silicon as described above and rigid polymers. Examples of rigid polymers include: polycarbonate, poly(L-lactide) (PLLA), poly(D,L-lactide) (PLA), polyglycolide (PGA), poly(L-lactide-co-D,L-lactide) (PLLA/PLA), poly (L-lactide-co-glycolide) (PLLA/PGA), poly(D,L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), polyD,L-lactide-co-caprolactone) (PLA/PCL), poly(glycolide-co-caprolactone) (PGA/PCL), polyanhydrides (PAN), poly(ortho esters), poly (phosphate ester), poly(amino acid), poly(hydroxy butyrate), polyacrylate, polyacrylamid, poly(hydroxyethyl methacrylate), polyurethane, polysiloxane and their copolymers.

Figure 3:
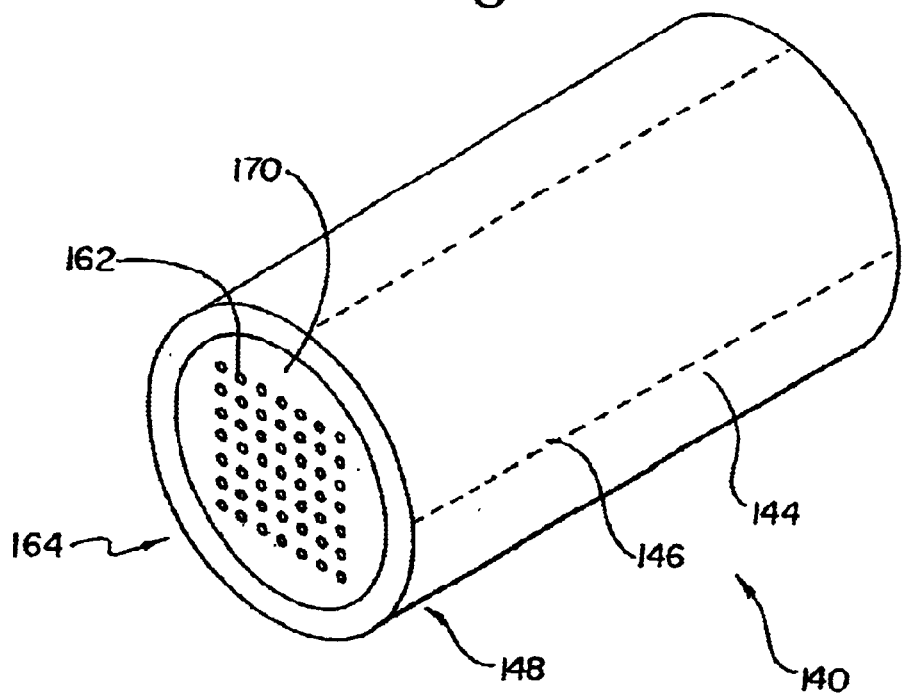
FIG. 3 is a perspective view of a second (needle-less) embodiment of the distal end of the injection catheter for use with the fluid delivery system illustrated in FIG. 1.

FIG. 3 is a perspective view of the distal end 148 of an alternative embodiment of an injection catheter 140 illustrating the needle-less embodiment. Injection catheter 140 is the same in form and function as catheter 40 and may be used in a similar manner, except as described below. As in the microneedle embodiment described previously, injection catheter 140 includes an elongate tubular member 144 defining a lumen 146. A nozzle member 170 is disposed within lumen 146 proximate distal end 148 of injection catheter 140. Nozzle member 170 defines a plurality of injection lumens 162. Injection lumens 162 collectively form an injection lumen array 164. Each injection lumen 162 is in fluid communication with lumen 146 of elongate tubular member 144. The injection lumens 162 may each have a diameter in the range of approximately 0.00005 to 0.005 inches.

Injection catheter 140 may be used in conjunction with the fluid delivery system 20 including the fluid source 52. The fluid source 52 is disposed proximate the proximal end of injection catheter 140 and is in fluid communication with lumen 146 of elongate tubular member 144. The fluid source 52 is capable of injection fluid into lumen 146 of elongate tubular member 144 at high pressure. The injection of fluid into lumen 146 of elongate tubular member 144 results in fluid being ejected from injection lumens 162.

In the needle-less embodiment of FIG. 3, fluid is ejected from injection lumens 162 with a velocity which is sufficient to inject the fluid into tissue disposed proximate the distal end 148 of injection catheter 140. This technique is commonly referred to as needle-less injection. A number of energy sources may be utilized to urge fluid into lumen 146 of elongate tubular member 144. Energy sources which may be suitable in some applications include springs and compressed gas. Preferably, a high pressure system is utilized as described in U.S. Pat. No. 5,697,901 to Eriksson, which is incorporated by reference.

FIG. 4 is a schematic view of the fluid delivery system 20 and a patient 74. Fluid delivery system 20 includes the injection catheter 40, the sheath 22, and the fluid source 52. Injection catheter 140 may be used in place of an injection catheter 40. An access catheter 80 is positioned with a distal end thereof positioned within a blood vessel 76. Access catheter 80 aids in the introduction of sheath 22 into blood vessel 76. Injection catheter 40/140 is disposed within lumen 26 of sheath 22. The distal end 48 of injection catheter 40/140 is positioned within the heart 78 of patient 74.

A method of injecting a fluid into tissue of the heart 78 of patient 74 is described with reference to FIG. 4. The fluid delivery system 20 may be navigated intravascularly or transthoracicly to heart tissue, but is described with reference to an intravascular approach for purposes of illustration only. Those of skill in the art will appreciate that the methods and devices of the present invention may be used to deliver therapeutic and/or diagnostic agents to other areas of the body without departing from the spirit and scope of the invention. For example, devices and methods in accordance with the present invention may be used to deliver fluid agents to esophageal varicies or to ulcers in the stomach lining.

The distal end of fluid delivery system 20 may enter the patient's vasculature at a convenient location such as a blood vessel in the neck or near the groin. Ideally, the distal end of fluid delivery system 20 will be atraumatic to reduce the probability that vascular tissues will be damaged as the catheter is advanced through the vascular system. To prevent damage to the vasculature, the distal end of injection catheter 40/140 may be retracted into lumen 26 of sheath 22.

Once the distal portion of fluid delivery system 20 has entered the patient's vascular system, the physician may urge distal end 28 of sheath 22 forward by applying longitudinal forces to hub 32 of sheath 22. Frequently, the path taken by sheath 22 through the vascular system is tortuous requiring sheath 22 to change direction frequently. While advancing sheath 22 through the torturous path of the patient's vasculature, the physician may apply torsional forces to the hub 32 to aid in steering sheath 22. To facilitate the steering process, the distal portion of sheath 22 may include a plurality of bends or curves. In some embodiments, it may be desirable to include a distal portion of sheath 22 which can be heated and bent to a desired shape, then allowed to cool.

To aid the physician in visualizing the vascular pathway, radiopaque contrast solution may be dispensed from distal end 28 of sheath 22 to enhance fluoroscopic visualization. In one method in accordance with the present invention, radiopaque contrast solution is urged through lumen 26 of sheath 22. Sheath 22 and injection catheter 40/140 may also include radiopaque markers. One example of a radiopaque marker is a band of radiopaque material disposed proximate the distal end of injection catheter 40/140 and/or sheath 22. Radiopaque bands of this type aid the physician in determining the location of the distal end of the device relative to the patient's anatomy. The radiopaque band may be comprised of a number of materials. Examples of materials which may be suitable in some applications include gold, platinum, tungsten, iron, silver, and thermoplastic material loaded with a radiopaque filler. Examples of radiopaque filler which may be suitable in some applications include barium sulfate, bismuth subcarbonate, bismuth trioxide, bismuth oxychloride, bismuth subcarbonate, tungsten powder, and depleted uranium.

Once distal end of 28 of sheath 22 is positioned proximate the target site, injection catheter 40/140 may be advanced so that nozzle member 70 contacts the bodily tissue at the target site. If injection catheter 40 with microneedles 60 is used, the microneedles 60 are advanced to penetrate the heart tissue. If injection catheter 140 with injection lumens 162 is used, the distal end of the injection array 164 is positioned adjacent the heart tissue surface. Force may then be applied to plunger 58 urging fluid out of fluid source 52 and into lumen 46/146 of injection catheter 40/140. The addition of fluid from fluid source 52 results in the injection of fluid into the target tissue via the injection array 164. The total fluid injected into the target tissue may be referred to as a dose. The dose is more readily retained in the heart tissue by utilizing the injection array 164.

A portion of the dose is dispensed from each injection lumen 162. The volume of fluid dispensed from each injection lumen 162 may be pre-selected. The pre-selected volume dispensed from each injection lumen may be a volume which can be rapidly absorbed and/or retained by the target tissue. By way of example, a dose of 100 microliters may be delivered via the injection array 164. The volume of fluid injected by each microneedle or injection lumen may be 0.1 to 20 microliters.

In an embodiment of the present invention, a low volume (several microliters but less than 100 microliters by a single injection) of solution is delivered to the heart such that it may absorb the delivered solution within the time frame of the injection. In contrast to higher volume injections, the heart is more capable of absorbing these low volumes. The effect of the low volume injection is to minimize expulsion by the tissue. In order to deliver the entire dose of virus, it may be desirable or necessary to concentrate the injection (i.e., deliver the same number of viral particles or micrograms of protein, typically delivered in 100 $\mu$l, in a volume of 10 $\mu$l) or keep the concentration of virus the same as that typically used, but increase the number of injections from 10 (typical) to 20, 30, or more.

Each injectate may also be delivered in a prolonged manner such that the heart can absorb the solution as it is being injected (rate of delivery$\leqq$rate of tissue absorption). For instance, the injection can be delivered at a defined flow rate using a syringe pump. The time of injection will depend on the volume to be delivered. For example, low volumes (a few microliters) may be delivered in under a minute while higher volumes (10 to 100 $\mu$l or more) may be delivered over several minutes. In this instance, it may be beneficial to include a method which gently attaches the injection catheter to the wall of the heart, for instance suction or vacuum.

If injection catheter 40 with mircroneedles 60 is used, the microneedles 60 may be left in the tissue for a period of time after the dose has been delivered to allow the fluid to be absorbed by the tissue. The amount of time required for the fluid to be absorbed by the tissue will vary depending on the volume of fluid delivered and the absorption characteristics of the tissue. The time period may be relatively short or prolonged, ranging, for example, from about 5 seconds to 2 minutes. Preferably, the time period ranges from about 5 seconds to about 30 seconds. When the mircroneedles 60 are subsequently withdrawn, leakage of the fluid from the tissue is further minimized or eliminated due to absorption thereof by the tissue.

The fluid injected into the tissue at the target area may include any number of therapeutic or diagnostic agents. Examples of therapeutic agents include genes, proteins, drugs, and caustic solutions. A radiopaque solution is an example of a diagnostic agent. Radiopaque solution may be used to mark an area. For example, when performing PMR, it may be desirable to mark the locations of wound formation.

Those of skill in the art will appreciate that when the organ being treated is the heart, fluid may be injected into the myocardium either from the epicardial or endocardial surface. In the exemplary embodiment of FIG. 4, the epicardial surface was accessed intravascularly by advancing a catheter through the vascular system. Other methods of have been envisioned in which the endocardial surface of the heart is accessed using surgical techniques such as transthoracic minimally invasive surgery.

Figure 5:
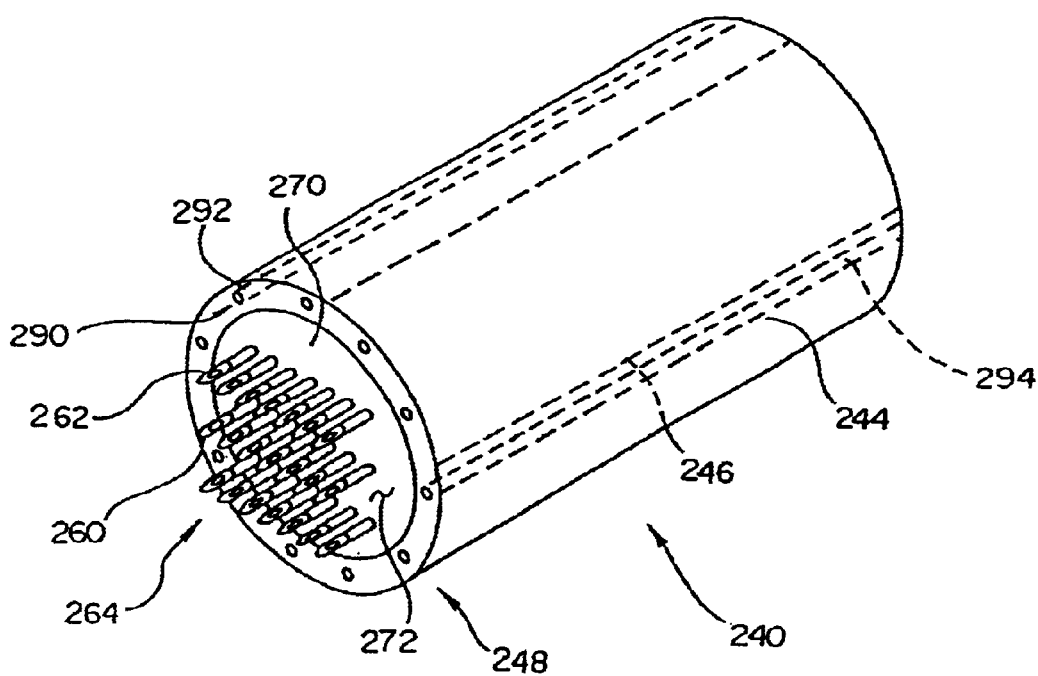
FIG. 5 is a perspective view of the distal end of the injection catheter incorporating an anchor for stabilization.

FIG. 5 is a perspective view of distal end 248 of an alternative embodiment of an injection catheter 240. Injection catheter 240 is the same in form and function as injection catheter 40 and may be used in the same manner, except as described below. Injection catheter 240 includes an elongate tubular member 244 defining a lumen 246. A plurality of anchors 290 are disposed proximate distal end 248 of injection catheter 240. During a procedure to inject a therapeutic agent into body tissue, anchors 290 may be utilized to retain distal end 248 of injection catheter 240 proximate the targeted tissue. In the embodiment of FIG. 5, each anchor 290 is comprised of a vacuum orifice 292. Each vacuum orifice 292 is in fluid communication with a vacuum lumen 294 defined by elongate tubular member 244.

Other embodiments of anchors 290 are possible without deviating from the spirit or scope of the present invention. For example, each anchor 290 may be comprised of an elongate wire with a helix disposed proximate its distal end. The helical end of the elongate wire may be "threaded" into the heart wall by rotating the wire. Additional examples, of anchors 290 which may be appropriate in some applications include hooks and barbs.

In the embodiment of FIG. 5, a nozzle member 270 is disposed within lumen 246 proximate distal end 248 of injection catheter 240. A plurality of microneedles 260 are disposed on a distal surface 272 of nozzle member 270. Nozzle member 270 and microneedles 260 define a plurality of injection lumens 262. Injection lumens 262 collectively form an injection lumen array 264. Each injection lumen 262 is in fluid communication with lumen 246 of injection catheter 240.

FIG. 6 is a schematic view of a fluid delivery system 220, including the injection catheter 240 of FIG. 5. Except as described below, fluid system 220 is the same in form and function as fluid system 20 and may be used in a similar manner. Fluid delivery system 220 includes the injection catheter 240, a sheath 222, a vacuum source 100, and a fluid source 252. A hub 232 is disposed at proximal end 230 of sheath 222, and a multi-port adapter 296 is disposed at the proximal end of injection catheter 240. Multi-port adapter 296 includes a plurality of ports 298. Fluid source 252 is in fluid communication with one port 298 of multi-port adapter 296. An access catheter 280 positioned with a distal end 288 positioned within blood vessel 276. Access catheter 280 may aid in the introduction of sheath 222 into blood vessel 276. Injection catheter 240 is disposed within a lumen of sheath 222. The distal end 248 of injection catheter 240 is positioned within the heart 278 of patient 274.

A method of injection a fluid into heart 278 of patient 274 is described with reference to FIG. 6. Sheath 222 is introduced into the vasculature of the patient 274 and it is urged forward until its distal tip is proximate the target tissue. Once the distal end of the sheath is positioned proximate the target site, injection catheter 240 may be advanced so that nozzle member contacts the bodily tissue at the target site. Anchors may then be activated to stabilize distal end 248 of injection catheter 240 during injection. Each anchor is comprised of a vacuum orifice 292 in fluid communication with a vacuum lumen. In this embodiment, anchors are activated by applying vacuum from vacuum source 100 to vacuum orifices via vacuum lumens and multi-port adapter 296. The vacuum orifaces apply suction to the surface of the tissue to stabilize the catheter 240 relative to the tissue.

With distal end 248 of injection catheter 240 anchored, force may be applied to plunger 258 urging fluid out of fluid source 252 and into lumen of injection catheter 240. The addition of fluid from fluid source 252 results in the injection of fluid into the target tissue via an injection array.

FIG. 7 is a cross sectional view of the distal portion of an alternative embodiment of fluid delivery system 320. Except as described below, fluid delivery system 320 is the same in form and function as fluid delivery system 220, and may be used in a similar manner. Fluid delivery system 320 includes a sheath 322 comprising an elongate tubular member defining a lumen 326. Sheath 322 also includes a distal end 328 and a proximal end. In the embodiment of FIG. 7, sheath 322 includes a hood portion 102 disposed proximate its distal end 328.

Fluid delivery system 320 also includes an injection catheter 340 which is slidingly disposed in lumen 326 of sheath 322. Injection catheter 340 includes a distal end 348, a proximal end, and an elongate tubular member 344 defining a lumen 346. A fluid source (not shown) is connected to proximal end of injection catheter 340.

A nozzle 370 is disposed proximate the distal end 348 of injection catheter 340. Nozzle 370 includes a plurality or microneedles 360. Each microneedle 360 defines an injection lumen 362 in fluid communication with lumen 346 of elongate tubular member 344. Injection lumens 362 collectively form an injection lumen array 364.

Sheath 322 and injection catheter 340 define an annular passage 108 disposed about injection catheter 340. Annular passage 108 terminates at an annular opening 110. Vacuum may be applied to annular passage 108 in order to anchor distal end 348 of injection catheter 340 to the bodily tissue at a desired target site. By doing so, the distal end of the sheath 322 and thus the distal end of the catheter 340 is stabilized relative to the heart tissue.

Figure 8:
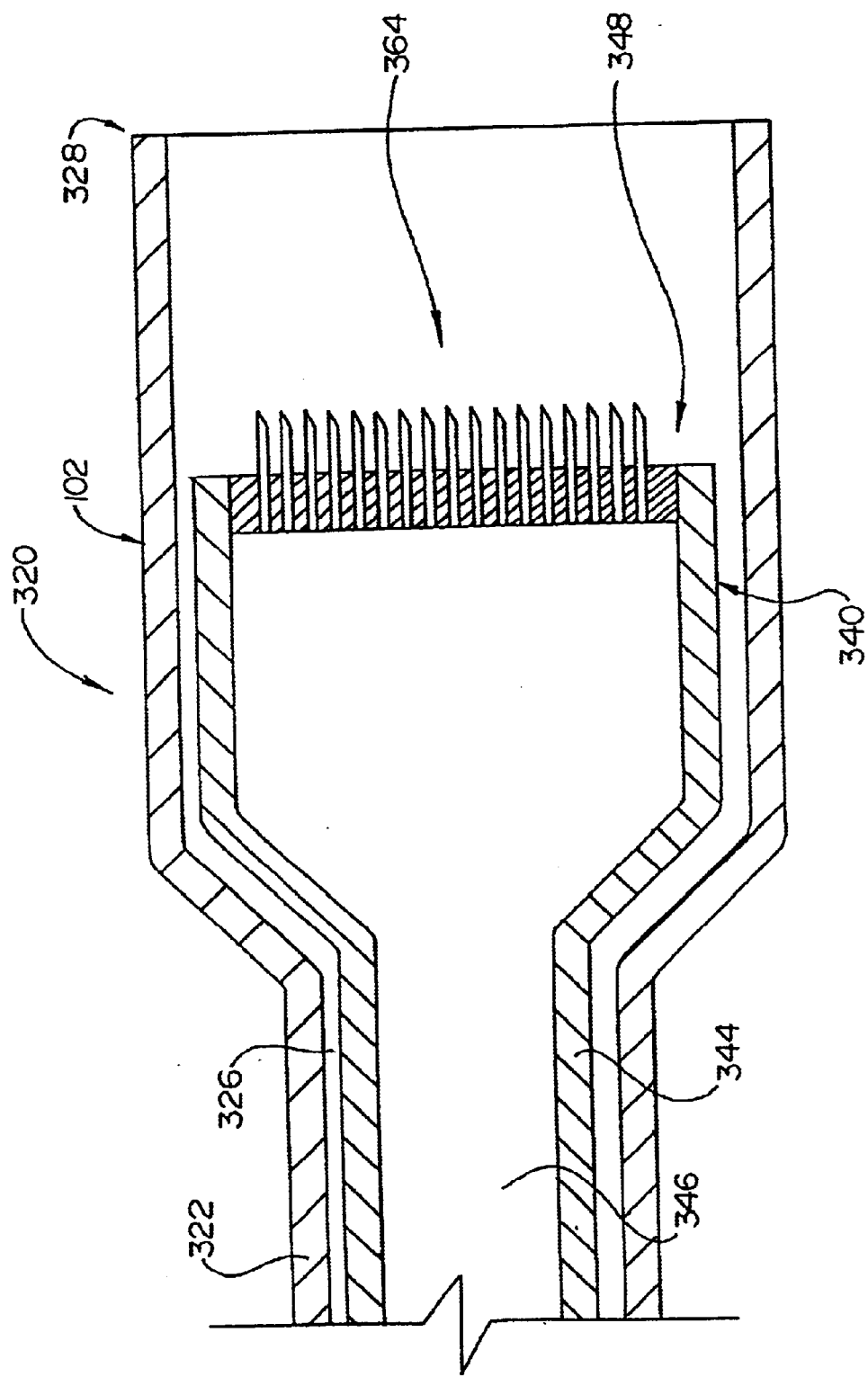
FIG. 8 is a cross sectional view of the fluid delivery system of FIG. 7, shown in the retracted position.

FIG. 8 is a cross sectional view of the distal portion of the fluid delivery system 320 illustrated in FIG. 7, shown in the retracted position. The distal end of injection catheter 340 has been retracted within hood portion 102 of sheath 322. The distal end 348 of injection catheter 340 is retracted within hood portion 102 of sheath 322 to reduce the probability that vascular damage will occur when fluid delivery system 320 is advanced through the vasculature of the patient. Upon positioning the system 320 at the target site, the catheter 340 may be advanced to the extended position as shown in FIG. 7.

With all embodiments described herein, the fluid injected into the target area may include any therapeutic or diagnostic agents needed to treat the medical condition which the physician is treating. It is to be appreciated that methods in accordance with the present invention may be used in the treatment of a number of medical conditions. For example, methods and devices of performing percutaneous myocardial revascularization (PMR) in accordance with the present invention have been envisioned.

A PMR procedure involves creating a plurality of wounds in hibernating tissue of the heart. These wounds are created by injecting a fluid into the tissue of the heart. As a result of these wounds, there will be increased blood flow to the myocardium caused in part by the body's healing response to the wounds. One healing response of the body is sometimes referred to as angiogenisis. In addition to promoting increased blood flow, it is also believed that PMR improves a patient's condition through denervation. Denervation is the elimination of nerves. The creation of wounds during this procedure may result in the elimination of nerve endings which were previously sending pain signals to the brain as a result of hibernating tissue.

Suitable wounds may be created by injecting a fluid such as water or saline into the heart tissue. Wound formation and revascularization of myocardial tissue may enhanced by injecting a fluid including a therapeutic agent into the tissue of the heart. Examples, of therapeutic agents which may be suitable include growth factors, drugs and caustic agents. The fluid injected into the heart tissue may also include a radiopaque material. Injecting a radiopaque material into the wound effectively marks the locations which have been treated. This will aid the physician in procedures which are being performed percutaneously using fluoroscopic equipment.

As describe above, injection catheters 40/140/240/340 may be used in the treatment of a number of medical conditions. By way of an additional example, injection catheters 40/140/240/340 may be used in the treatment of esophageal varicies, a condition where blood vessels of the esophagus are enlarged and may potentially burst. For such a procedure, the array of injection orifices is disposed proximate the enlarged varix and an appropriate agent is injected into the varix. When treating an esophageal varice, the agent may be a coagulant such as sodium morrhuate. When a coagulant is injected into a varix, it causes the occlusion thereof.

Although treatment of the heart is used as an example herein, the medical devices of the present invention are useful for treating any mammalian tissue or organ. Non-limiting examples include tumors; organs including but not limited to the heart, lung, brain, liver, kidney, bladder, urethra and ureters, eye, intestines, stomach, pancreas, ovary, prostate; skeletal muscle; smooth muscle; breast, cartilage and bone.

The terms "therapeutic agents" and "drugs" are used interchangeably herein and include pharmaceutically active compounds, cells, nucleic acids with and without carrier vectors such as lipids, compacting agents (such as histones), virus, polymers, proteins, and the like, with or without targeting sequences.

Specific examples of therapeutic agents used in conjunction with the present invention include, for example, proteins, oligonucleotides, ribozymes, anti-sense genes, DNA compacting agents, gene/vector systems (i.e., anything that allows for the uptake and expression of nucleic acids), nucleic acids (including, for example, recombinant nucleic acids; naked DNA, cDNA, RNA; genomic DNA, cDNA or RNA in a non-infectious vector or in a viral vector which may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic polymers that are selected from a number of types depending on the desired application. Other pharmaceutically active materials include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitorfurantoin; anesthetic agents such as lidocaine, bupivacaine, and ropivacaine; nitric oxide (NO) donors such as lisidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptidecontaining compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; survival genes which protect against cell death, such as anti-apoptotic Bcl-2 family factors and Akt kinase; and combinations thereof.

Examples of polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins useful in the present invention include, without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

The present invention is also useful in delivering cells as the therapeutic agent. Cells can be of human origin (autologous or allogeneic) or from an animal source (xenogeneic), genetically engineered if desired to deliver proteins of interest at a delivery or transplant site. The delivery media is formulated as needed to maintain cell function and viability.

Having thus described the preferred embodiments of the present invention, those of skill in the art will readily appreciate that yet other embodiments may be made and used within the scope of the claims hereto attached. Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A catheter for delivering a therapeutic to target tissue within the body of a patient, comprising:
   a flexible elongate tubular member having a proximal end, a distal end, and a lumen extending therethrough; and
   a nozzle member disposed proximate the distal end of the tubular member, the nozzle member including an injection array at a distal end of the nozzle member,
   the injection array comprising a plurality of injection orifices, each injection orifice fluidly coupled to the lumen of the elongate tubular member,
   the orientation of the injection orifices being fixed relative to each other.

2. The catheter of claim 1, further comprising:
   an outer sheath having a proximal end, a distal end, and a lumen extending therethrough
   wherein the tubular member is slidingly disposed in the lumen of the sheath.

3. The catheter of claim 2, further comprising:
   an anchor disposed at an end of the sheath.

4. The catheter of claim 3, wherein the anchor comprises a vacuum orifice.

5. The catheter of claim 4, wherein the vacuum orifice is in fluid communication with a vacuum source via the lumen of the elongate tubular member.

6. The catheter of claim 2, wherein the sheath further comprises:
   a hood disposed at the distal end of the sheath.

7. The catheter of claim 6, wherein the distal end of the elongate tubular member may be retracted within the hood.

8. The catheter of claim 2, further comprising:
   a fluid source in fluid communication with the lumen of the sheath.

9. The catheter of claim 2, wherein the sheath further comprises:
   a support member disposed around the elongate tubular member.

10. The catheter of claim 2, wherein the sheath is made of polyether block amide.

11. The catheter of claim 1, wherein each injection orifice is positioned at an end of a micro-needle, the micro-needle coupled to the lumen.

12. The catheter of claim 11, wherein the micro-needle is slidably placed in the nozzle member.

13. The catheter of claim 11, wherein the micro-needle has a penetrating length of approximately 0.5 to 5 mm.

14. The catheter of claim 1, wherein the orifices are an open end of a plurality of injection lumens defined by the nozzle member.

15. The catheter of claim 14, wherein the orifices have a diameter of approximately 0.00005 to 0.005 inches.

16. The catheter of claim 1, wherein the target tissue is the heart.

17. The catheter of claim 1, wherein the elongate tubular member is made of polytetrafluoroethylene.

18. The catheter of claim 1, wherein the elongate tubular member is made of material having a low-friction surface.

19. The catheter of claim 1, further comprising an anchor disposed proximate the distal end of the tubular member.

\* \* \* \* \*

UNITED STATES PATENT AND TRADEMARK OFFICE
CERTIFICATE OF CORRECTION

PATENT NO. : 6,689,103 B1
DATED : February 10, 2004
INVENTOR(S) : Maria Palasis

It is certified that error appears in the above-identified patent and that said Letters Patent is hereby corrected as shown below:

Column 2,
Line 19, change "lesion" to -- lesions --;

Column 3,
Lines 50-51, change "transthoracicly" to -- transthoracically --;

Column 4,
Line 29, change "drawings" to -- drawings, --;
Line 57, change "of support" to -- of the support --;

Column 6,
Lines 27-28, change "polyD,L-lactide-co-caprolactone)" to -- poly(D,L-lactide-co-caprolactone) --;

Column 7,
Line 16, change "transthoracicly" to -- transthoracically --;
Line 24, change "varicies" to -- varices --;

Column 8,
Lines 50 and 59, change "mircroneedles" to -- microneedles --;

Column 9,
Line 33, change "examples," to -- examples --;
Line 56, change "280 positioned" to -- 280 is positioned --;

Column 10,
Line 9, change "orifaces" to -- orifices --;
Line 33, change "or" to -- of --;

UNITED STATES PATENT AND TRADEMARK OFFICE
CERTIFICATE OF CORRECTION

PATENT NO.   : 6,689,103 B1
DATED        : February 10, 2004
INVENTOR(S)  : Maria Palasis It is certified that error appears in the above-identified patent and that said Letters Patent is hereby corrected as shown below:

Column 11,
Line 5, change "angiogenisis" to -- angiogenesis --;
Line 20, change "wound" to -- wounds --;
Line 24, change "describe" to -- described --;
Line 28, change "varicies" to -- varices --;
Line 62, change "viral, liposomes" to -- viral liposomes --;

Column 12,
Line 16, change "nitorfurantoin" to -- nitrofurantoin --;
Line 18, change "lisidomine" to -- linsidomine --;
Line 24, change "Warafin" to -- Warfarin --;
Line 37, change "endogeneus" to -- endogenous --; and,
Line 62, change "insulin like" to -- insulin-like --.

Signed and Sealed this

Twentieth Day of July, 2004

JON W. DUDAS
*Acting Director of the United States Patent and Trademark Office*